Figure 1:
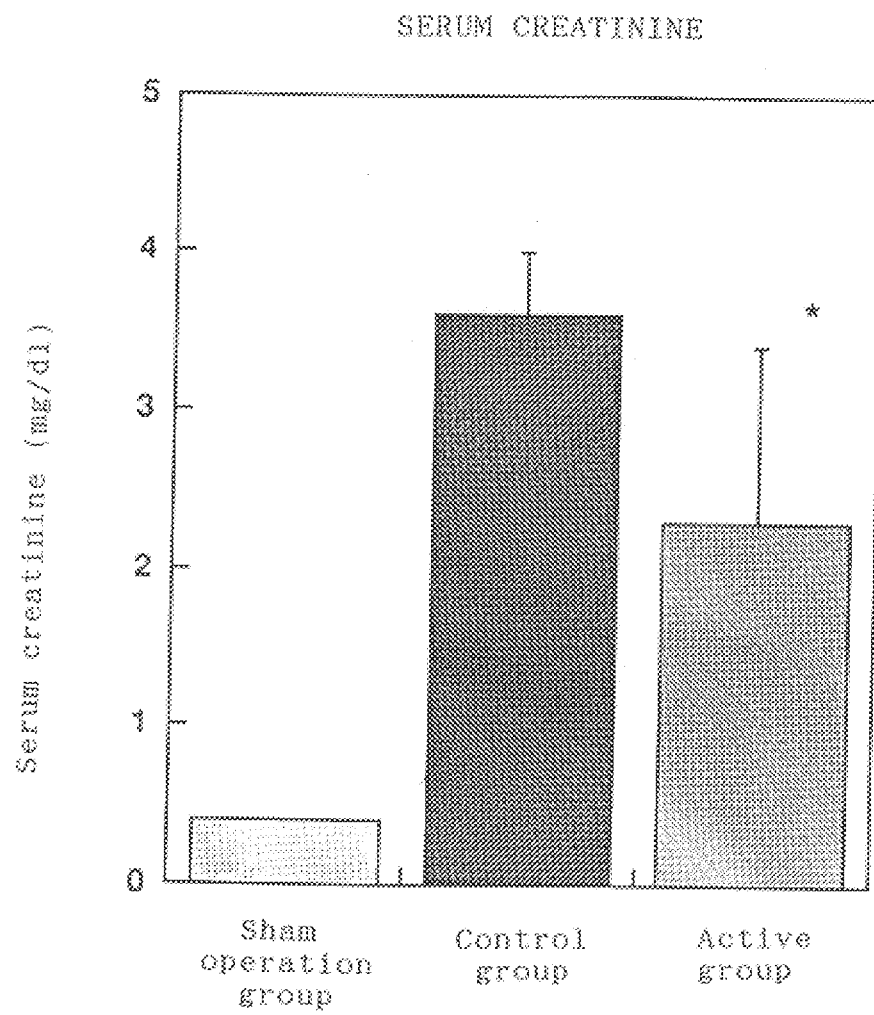

United States Patent [19]
Ota et al.

[11] Patent Number: 5,843,969
[45] Date of Patent: Dec. 1, 1998

[54] PROTECTING AGENT FOR ORGAN OR TISSUE

[75] Inventors: Mikio Ota; Hideki Horiuchi; Shigehisa Kitahara; Shiro Kondo; Yasuhiro Takano, all of Hino, Japan

[73] Assignee: Teijin Limited, Osaka, Japan

[21] Appl. No.: 737,406

[22] PCT Filed: Apr. 4, 1996

[86] PCT No.: PCT/JP96/00924

§ 371 Date: Nov. 12, 1996

§ 102(e) Date: Nov. 12, 1996

[87] PCT Pub. No.: WO96/31211

PCT Pub. Date: Oct. 10, 1996

[30] Foreign Application Priority Data

Apr. 7, 1995 [JP] Japan .................................. 7-082576

[51] Int. Cl.⁶ .................................................. A61K 31/44
[52] U.S. Cl. ............................................................ 514/345
[58] Field of Search ............................................. 514/365

[56] References Cited

U.S. PATENT DOCUMENTS 5,124,342  6/1992  Kerdesky et al. ....................... 514/369

FOREIGN PATENT DOCUMENTS

| 2039458 | 10/1991 | Canada . | |
| 0 513 379 B1 | 9/1996 | European Pat. Off. | A61K 31/425 |
| 3-157385 | 7/1991 | Japan | C07D 487/04 |
| 5-320072 | 12/1993 | Japan . | |
| 93/08819 | 5/1993 | WIPO . | |

OTHER PUBLICATIONS

Oshima et al. GI Res., vol. 2, No. 5, pp. 517–521, 1994,.
English language translation of JP 5–320072, 1993.
Wakabayashi et al., GI Res, vol. 2, No. 5, pp. 531–537, 1994.
Yamasaki et al., Acta Neurochir [suppl] 60:300–302, 1994.
Sakio et al., Dokkyo Igakkai Zasshi (Dokkyo Igakukai Zasshi) vol. 8, No. 2, pp. 279–284, 1993.
Suzuki et al., Cyto–protection Biol, vol. 7, pp. 425–431, 1989.
Sohara, Igaku no Aymumi vol. 157, No. 5, pp. 301–304, 1991.
Chem. Abs. 117(15):149304u, Carmichael et al, 1991.
Chem. Abs. 119(3):20519e, Rothwell, 1993.
Atshushi et al., GI Res. vol. 2, No. 5, pp. 517–521 (Abstract only), 1994.
Chem. Abs. 120(20): 253384t, Yamazaki, et al, 1993.
Wakabayashi, et al. GI Res., vol. 2, No. 5, pp. 531–537 (Abstract only), 1994.
Yamasaki et al. Acta Neurochirurgica Supplementum—Wien–, vol. 60, pp. 200–302 (Abstract only), 1994.
Hideaki et al., Dokkyo Igakkai Zasshi, vol. 8, No. 2 pp. 279–284 (Abstract only), 1993.
Shigehiko et al., Cyto–protection Biol, vol. 7, pp. 425–431 (Abstract only), 1989.
Yasunori, Igaku no Ayumi, vol. 157, No. 5, pp. 301–304 (Abstract only), 1991.
Journal of Clinical Investigation, 1984, 74, 1156–1164.
European Journal of Pharmacology, 1987, 140, 203–207.
Hepatology, 1988, 8(3), 580–584.
Research in Experimental Medicine, 1993, 193, 275–283.

Primary Examiner—Raymond Henley, III
Attorney, Agent, or Firm—Sughrue, Mion, Zinn, Macpeak & Seas, PLLC

[57] ABSTRACT

An agent composition for the therapy or prevention of the injury of an organ or a tissue containing a phenylthiazole derivative expressed by the following formula (1):

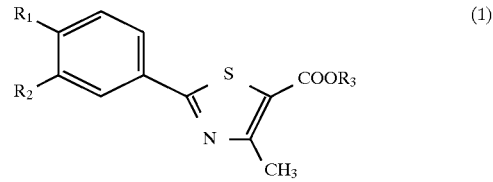

(1)

($R_1$ is a $C_1$–$C_{18}$ alkoxy group or a cyclic amino group; $R_2$ is a cyano group or a nitro group; $R_3$ is a hydrogen atom or a $C_1$–$C_4$ alkyl group), and/or its salt as an active ingredient.

6 Claims, 6 Drawing Sheets

* : $p<0.05$
** : $p<0.01$
*** : $p<0.001$

PROTECTING AGENT FOR ORGAN OR TISSUE

This application is a 371 of PCT/JP96/00924 filed Apr. 4, 1996.

TECHNICAL FIELD

This invention relates to a therapeutic agent or preventing agent for various kinds of diseases associated with an injury caused by active oxygen generated after ischemia-reperfusion.

TECHNICAL BACKGROUND

In recent years, it has been found that large amount of active oxygen is generated in an ischemic state and subsequent reperfusion of blood in various kinds of organs including heart, and this is one of the factors to induce various kinds of diseases. That is, when blood flow is blocked in a blood vessel by a thrombus, etc., the ischemic state occurs in the controlling region of the blood vessel. In this case, the oxygen supply to the tissue in the region is intercepted and accordingly the tissue falls in a dangerous state. When this state lasts for a certain length, the tissue runs into a necrotic state. Once this occurs, the recovery is impossible. Therefore, it is important that the reperfusion of blood is achieved at the earliest opportunity to save the tissue before it is suffered from permanent damage.

However, even the reperfusion is started before the necrosis of the tissue, the reperfusion itself has harmful effects on the tissue in a hypoxia state. This phenomenon is called ischemia-reperfusion injury.

In a normal state, xanthine and hypoxanthine, metabolites of nucleic acids, exist each in cells at a low concentration and are converted into nucleic acid with xanthine hydrogenase. However, in an ischemic state, the synthesis of ATP is lowered. Accordingly, ADP and AMP are accumulated and, the contents of xanthine and hypoxanthine, metabolites of nucleic acid, increase significantly. Further, when the reperfusion of blood is initiated, the xanthine hydrogenase is converted into xanthine oxidase. The produced xanthine oxidase metabolizes the xanthine and hypoxanthine to uric acid with oxygen which works as an electron receptor. This process produces a large amount of oxygen-anion radicals ($O^{2-}$) as by-product. The oxygen-anion radical is the active oxygen, which carries one of the factors causing the ischemia-reperfusion injury. Further, it is considered that other active oxygen species such as hydrogen peroxide and hydroxy radical are secondarily produced and the injury is aggravated.

On the other hand, it is known that the active oxygen is generated from leukocyte through other path besides this. That is, in an ischemic state, the leukocyte is activated by a chemical mediator such as leukotriene, accumulates at the ischemic sites and generates active oxygen there. Accordingly, it plays an important role on the ischemia-reperfusion injury.

The generation of active oxygen is considered to affect aggravation of prognosis in various kinds of ischemic diseases including myocardial infarction and others such as cerebral infarction, pulmonary thromboembolism, thrombosis in other various organs, etc. Similarly, it is pointed out that the generation of active oxygen is affecting aggravation of prognosis in various kinds of operations such as coronary artery bypass operation which need to block blood flow temporarily, percutaneous transluminal coronary angioplasty, injuries during the application of a thrombolytic agent, various kinds of operations and treatments during organ transplantation, etc. Therefore, a substance suppressing the generation of active oxygen is considered to be useful for the prevention of these injuries.

Until now, as substances suppressing the generation of active oxygen, allopurinol, which is an inhibitor of xanthine oxidase and used as a therapeutic agent for gout and a xanthine oxidase inhibitor disclosed in Japanese Unexamined Patent Publication (Kokai) No. 3-157385 have been studied from the view point of suppressing effect against organ injuries caused by ischemia-reperfusion. However, the results of the animal experiments using an ischemia-reperfusion injury model are divided into two groups: an effective group (Journal of Clinical Investigation, 1984, 74, 1156–1164 and European Journal of Pharmacology, 1987, 140, 203–207) and a group in which effect is not clear (Hepatology, 1988, 8(3), 580–584 and Research in Experimental Medicine, 1993, 193, 275–283), and no clear conclusion has been obtained yet. In fact, so far, they have practically not been used.

Besides these compounds, SOD, etc., are under development as an agent for depleting the generated active oxygen but until now, none of them has become into use.

Further, a phenylthiazole derivative expressed by the following formula (1):

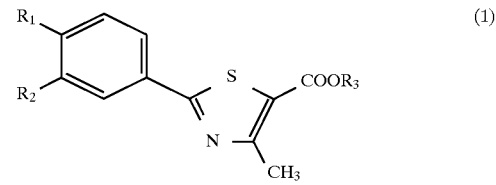

(wherein $R_1$ is a $C_1$–$C_8$ alkoxy group or a cyclic amino group, $R_2$ is a cyano group or a nitro group, $R_3$ is a hydrogen atom or a $C_1$–$C_4$ alkyl group), exhibits strong xanthine oxidase inhibiting activity and is used as a therapeutic agent for hyperuricemia and gout (International Publication W092/09279). However, it is not known what kind of effect the compound expressed by the above formula (1) has on the ischemia-reperfusion injury of various kinds of organs caused by the generation of active oxygen.

Therefore, the issue that the present invention intends to solve is to obtain a therapeutic agent or a preventing agent against various kinds of diseases involved in injuries caused by the active oxygen generated after the ischemia-reperfusion, etc.

DISCLOSURE OF INVENTION

The present inventors engaged in researches on what kinds of influences the compounds expressed by the above formula (1) have on ischemia-reperfusion injury and found that they have suppressing activity against the injury of an organ or a tissue associated with ischemia-reperfusion injury and further have suppressing activity against the production of chemical mediators activating leukocytes which play a part in the ischemia-reperfusion injury. The present invention was accomplished based on these findings.

Therefore, the present invention provides a therapeutic or a preventing agent composition against the injury of an organ or a tissue, which contains a phenylthiazole derivative expressed by the following formula (1):

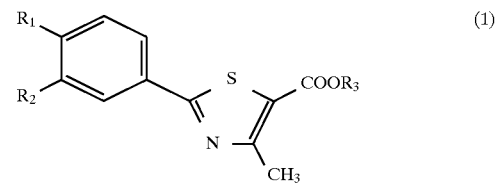

(wherein $R_1$ is a $C_1$–$C_8$ alkoxy group or a cyclic amino group, $R_2$ is a cyano group or a nitro group, $R_3$ is a hydrogen atom or a $C_1$–$C_4$ alkyl group), and/or its salt as an active component.

Further, the present invention provides a therapeutic, preventing or prophylactic method against the injury of an organ or a tissue based on the use of the phenylthiazole derivative expressed by the above formula (1).

Furthermore, the present invention provides the use of the phenylthiazole derivative expressed by the above formula (1) for therapy, prevention or prophylaxis of the injury of an organ or a tissue.

BRIEF EXPLANATIONS FOR THE FIGURES

The FIG. 1 shows the effect of the administration of the active component of the agent of the present invention on serum Cre value in the renal ischemia-reperfusion injury model in rats.

Figure 2:
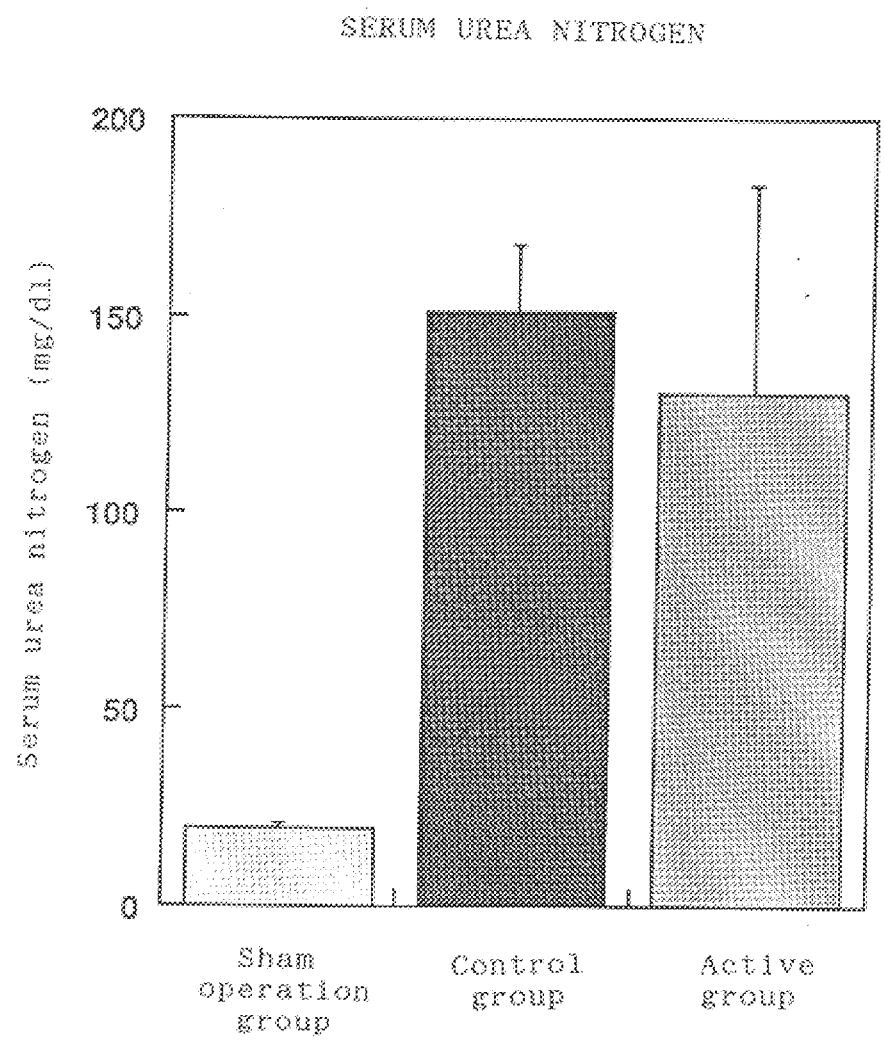

The FIG. 2 shows the effects of the administration of the active component on serum BUN value in the renal ischemia-reperfusion injury model in rats.

Figure 3:
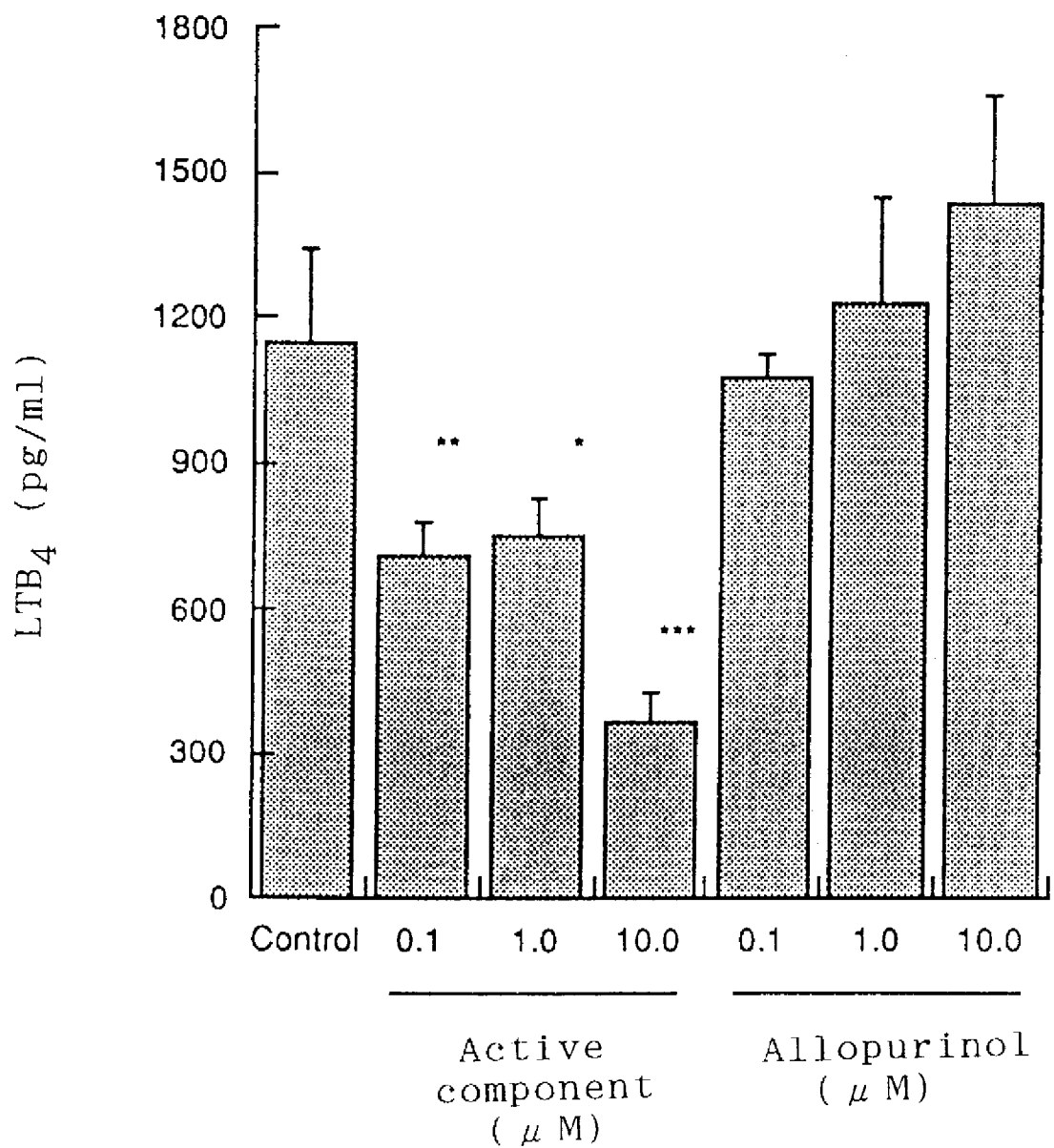

The FIG. 3 shows the effect of the administration of the active component on leukotriene-$B_4$ production in cultured cells.

Figure 4A:
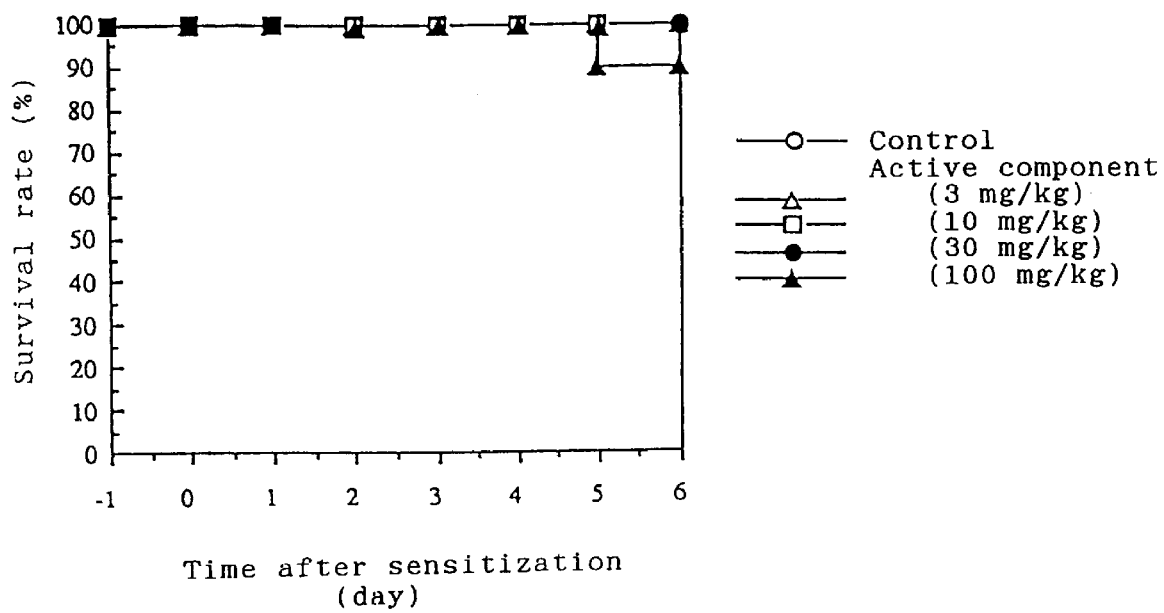
Figure 4B:
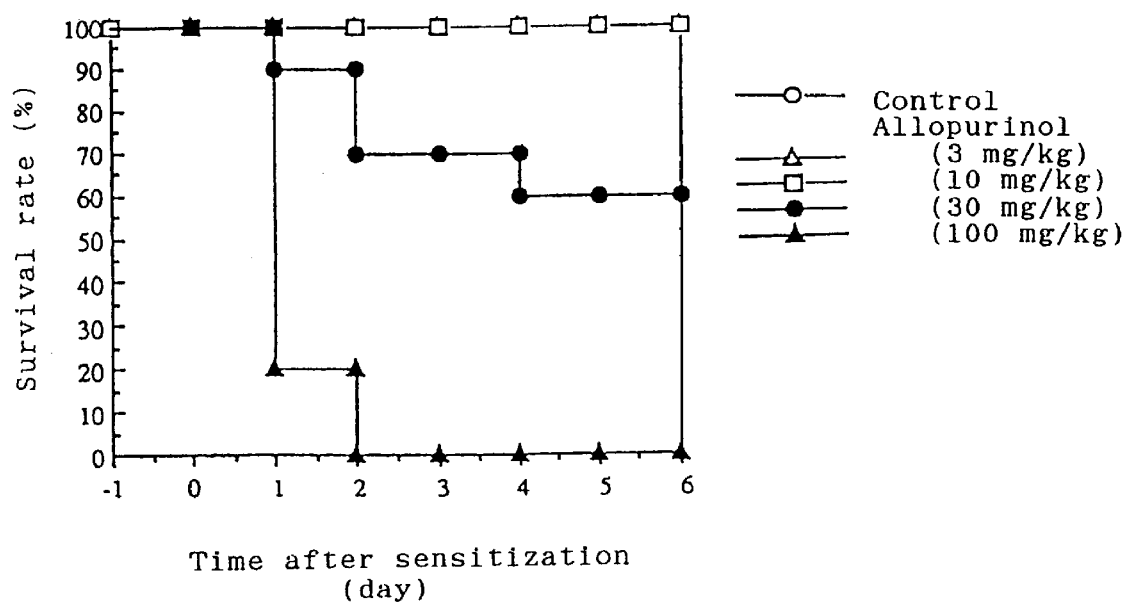

The FIGS. 4A and 4B show the effect of the administration of the active component on survival rate in DNFB-sensitized mice.

Figure 5A:
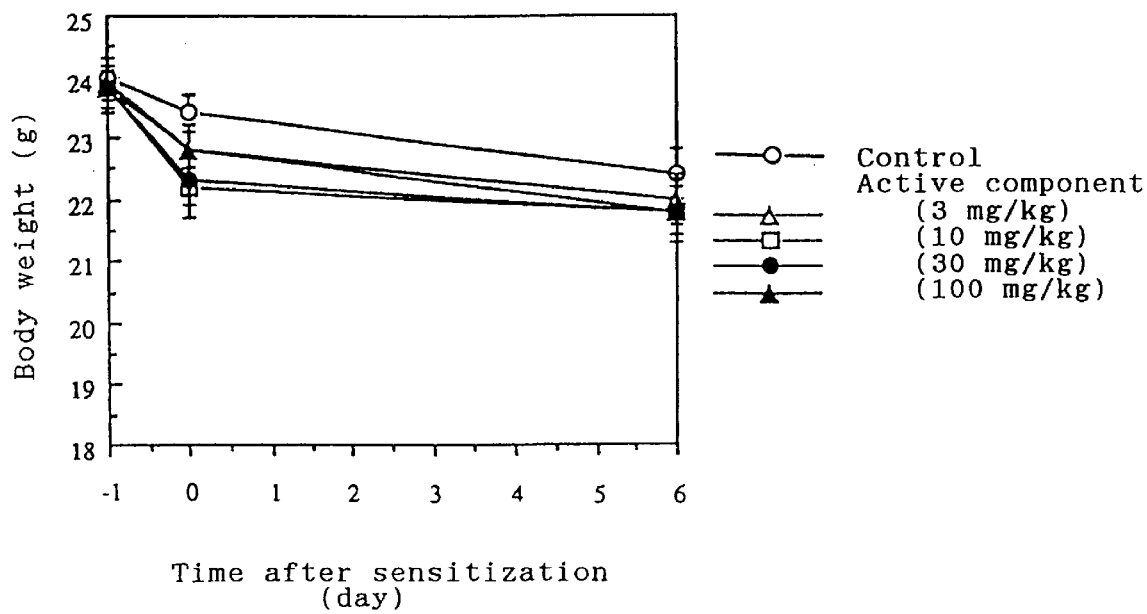
Figure 5B:
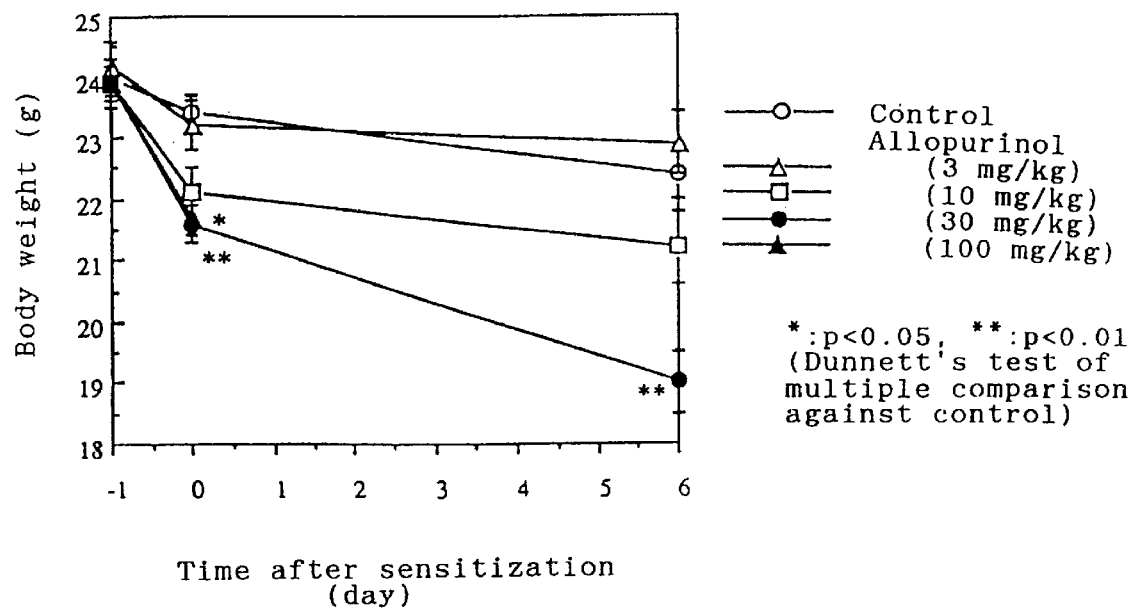

The FIGS. 5A and 5B show the effect of the administration of the active component on body weight in DNFB-sensitized mouse.

Figure 6:
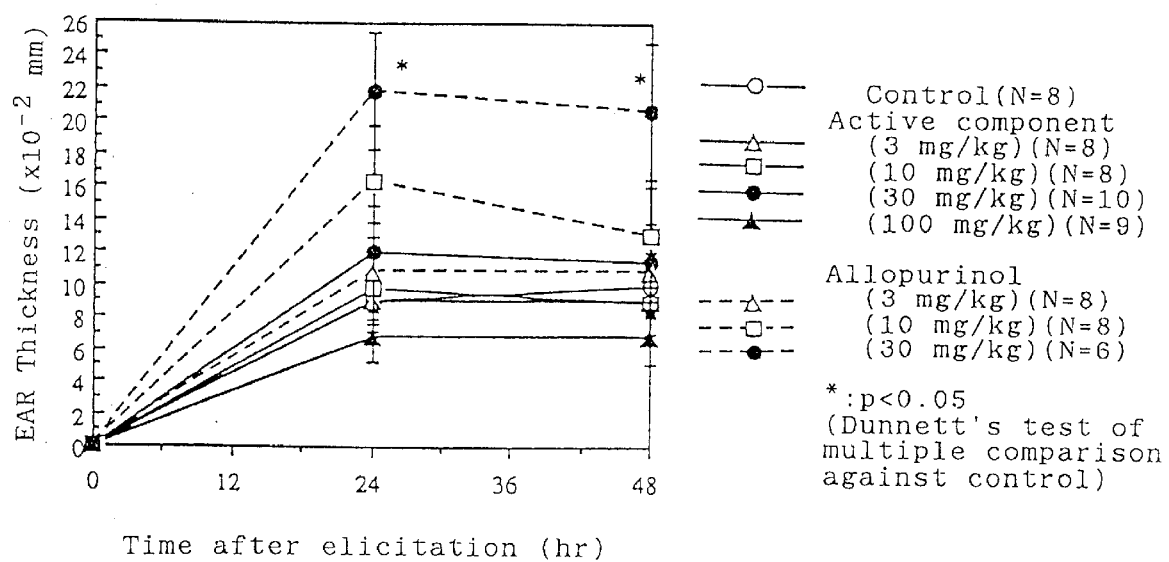

The FIG. 6 shows the effect of the administration of the active component on variation of the ear thickness with time after the elicitation of an immunological reaction in DNFB-sensitized mouse.

PREFERRED EMBODIMENTS OF THE INVENTION

In the above formula (1), $R_1$ is a $C_1$–$C_8$ alkoxy group or a cyclic amino group. Examples of the $C_1$–$C_8$ alkoxy group include methoxy, ethoxy, propoxy, isopropoxy, butoxy, isobutoxy, tert-butoxy, pentyloxy, isopentyloxy, hexyloxy and octyloxy groups. Further, examples of the cyclic amino group include pyrrolidino, piperidino, morpholino and piperazinyl groups. Above all, a $C_2$–$C_6$ alkoxy group is preferred as the $R_1$, and an isobutoxy group is particularly preferred.

Further, $R_2$ is a cyano group or a nitro group, and the cyano group is preferred as the $R_2$.

Furthermore, $R_3$ is a hydrogen atom or a $C_1$–$C_4$ alkyl group. Examples of the $C_1$–$C_4$ group include methyl, ethyl, propyl, isopropyl, butyl and isobutyl groups. Above all, a methyl group is preferred.

For application, these active components are formulated into an oral preparation such as a soft capsule, a hard capsule, a tablet or syrup, an injection or an external preparation with a known method by using an appropriate diluent, etc.

Examples of the diluent include a vegetable oil (e.g. corn oil, cottonseed oil, coconut oil, almond oil or peanut oil), an oily ester such as a middle-chain fatty-acid glyceride, a mineral oil, vaseline, an animal oil or fat, a cellulose derivative (a crystalline cellulose, hydroxypropylcellulose, hydroxypropylmethylcellulose or methylcellulose), polyvinyl pyrrolidone, dextrin, lactose, mannitol, sorbitol and starch.

A dose of the active component is usually about 0.1–300 mg/day, preferably 1–50 mg/day, and it is usually administered 1–3 times/day. The preparation is preferably formulated so that it can satisfy these conditions.

Further, for the safety evaluation of the agent of the present invention, an acute toxicity test is carried out with rats in terms of 2-(3-cyano-4-isobutyloxyphenyl)-4-methyl-5-thiazolecarboxylic acid as the active component. None of rats died by a single oral administration up to 300 mg/kg.

The active component of the agent of the present invention expressed by the formula (1) can be synthesized e.g. by the method described in the International Publication WO92/09279.

The agent of the present invention can be used for therapy or prevention of the injury of an organ or a tissue. Examples of the injuries of an organ or a tissue include diseases associated with the ischemia-reperfusion injury of an organ. For instance, the agent can be used against the disease associated with the ischemia-reperfusion injury of an organ caused by the generation of activated oxygen. Concretely, examples of the diseases include diseases associated with the ischemia-reperfusion injury in heart, liver, brain, kidney, digestive canals and lung caused by the generation of active oxygen.

EXAMPLES

The present invention will be explained further in detail hereafter with examples.

Example 1

Tablets each consisting of the following composition were prepared.

| | |
|---|---|
| 2-(3-Cyano-4-isobutyloxyphenyl)-4-methyl-5-thiazolecarboxylic acid | 50 mg |
| Lactose | 230 mg |
| Potato starch | 80 mg |
| Polyvinyl pyrrolidone | 11 mg |
| Magnesium stearate | 5 mg |
| Total weight | 376 mg |

The phenylthiazole derivative, lactose and potato starch were well mixed, and the mixture was homogeneously moistened with a 20% polyvinyl pyrrolidone solution in ethanol. Subsequently, this was passed through a 20 mesh sieve, dried at 45° C., and then passed once again through a 15 mesh sieve. The obtained granules were mixed with magnesium stearate, and compressed into tablets.

Example 2

An ischemia-reperfusion injury model of kidney for studying effect on the ischemia-reperfusion injury was prepared with a rat as shown below, and the effect of the administration of the active component of the agent of the present invention was studied by using the model animal.

The abdomen of an SD rat (male, 6 weeks of age) was opened under anesthesia with sodium pentobarbital, the separated left and right renal arteries were clamped with arterial clips to block the blood flow completely, and the kidneys were brought into an ischemic state. After 60-minute ischemia, the artery clamps were released, and blood flow was restarted to bring the kidneys to a reperfused state. After the suture of the opened abdomen, the animal was returned to a cage and allowed to have free access to food and water. After 24-hour reperfusion, the abdomen was opened under ether anesthesia and a blood sample was drawn from abdominal aorta.

Serum was separated from the obtained blood sample by centrifugation. Blood urea nitrogen (BUN) level and serum creatinine (Cre) level, a parameter for kidney function injury, were determined on the serum using an automated analyzer (Hitachi 7070) by an urease-indophenol method and Jaffe method, respectively.

2-(3-Cyano-4-isobutyloxyphenyl)-4-methyl-5-thiazolecarboxylic acid, the active component, was suspended in a 0.5% methylcellulose aqueous solution. The active component was orally administered to each ischemia-reperfusion injury model animal at a dose of 50 mg/kg in a 4-ml suspension 60 min prior to the ischemic state. At the same time, 4 ml of the 0.5% methylcellulose aqueous solution, the solvent for the active component, was orally administered to each of animals of a control group and a sham-operation group. Numbers of animals in the sham-operation group, the control group and the active component group were 7, 6 and 6, respectively. The results were each expressed as the mean ± standard deviation. Tests of significant difference against the control group were performed using Welch's t-test.

The result of the serum Cre measurement is shown in FIG. 1. The serum Cre level of the rats of the ischemia-reperfusion operation group (control group) was 3.6±0.4 mg/dl and this was clearly higher than that (0.4±0.0) of the rats of the sham-operation group. Compared with the control group, the increase of the serum Cre level in the rats administered with the active component was significantly suppressed (2.3±1.1, $p<0.05$).

The result of the serum BUN measurement is shown in FIG. 2. The serum BUN level of the rats of the ischemia-reperfusion operation group (control group) was 151.3±16:8 mg/dl and this was clearly higher than that (19.3±1.7) of the rats subjected to the sham-operation. Compared with the control group, the rats administered with the active component exhibited a tendency to suppress the increase of the serum BUN.

Example 3

The effect of the agent of the present invention on the production of leukotriene, which is one of the strong chemical mediators against leukocytes and is thought to be associated with the pathology of the ischemia-reperfusion injury, was investigated by means of cultured cells. RBL-1 cells (Dainippon Pharmaceutical Co.) were cultured in a Dulbecco's Modified Eagle's Medium containing fetal bovine serum in an amount of 10%. The cultured cells were adjusted to $5\times10^6$ cells/ml. The solution of 2-(3-cyano-4-isobutyloxyphenyl)-4-methyl-5-thiazolecarboxylic acid, the active component of the agent of the present invention, or allopurinol as a control in dimethyl sulfoxide was added into 1 ml of the cell suspension. After incubated at 37° C. for 5 min, this was immersed into ice and kept for 10 min. Subsequently, $2\times10^{-5}$ mol of A23187, Ca-ionophore, was added to the chilled cell suspension to make the final concentration of 25 mM, and the cell suspension was incubated again at 37° C. for 15 min. Further, the suspension was held in ice for 10 min. The suspension was subjected to centrifugation at 3000 rpm for 10 min and the cells were removed. Leukotriene $B_4$ ($LTB_4$) level in the supernatant was measured by enzyme immunoassay. The results were each expressed as the mean ± standard deviation. A significant difference test against the control group was carried out using Bonferroni's test of a multiple comparison.

The result of $LTB_4$ measurement is shown in FIG. 3. As can be seen from the figure, the addition of the phenylthiazole derivative, the active component of the agent of the present invention, in an amount of $1\times10^{-8}$ mol (final concentration of 10 $\mu$M) suppresses the production of $LTB_4$ significantly ($p<0.001$). On the other hand, the addition of allopurinol in an amount of up to $1\times10^{-8}$ mol (final concentration of up to 10 $\mu$M) had no effect on the production.

Example 4

Allopurinol, which is an inhibitor of xanthine oxidase and used as a therapeutic agent for gout, is known that it has side effects including an allergy reaction during clinical application and occasionally the side effect is so severe that the patient is brought to death (The Journal of Medicine, 1984, 76, 47–56; The Annals of Pharmacotherapy, 1993, 27, 337–343), and accordingly careful caution is required on the clinical application. Therefore, the presence of such side effects was examined on the active component of the agent of the present invention by using a mouse allergic dermatitis model.

Hair was removed from the abdomen to the breast of a BALB/c mouse (male, 8 weeks of age) with hair clippers and a shaver. A 0.5% dinitro-fluorobenzene (DNFB) ethanol solution (100 $\mu$l head/day) was applied on the hair-removed part one day and two days after the removal of hair to establish sensitization. 2-(3–Cyano-4-isobutyloxyphenyl)-4-methyl-5-thiazolecarboxylic acid, the active component of the present invention, and allopurinol are each suspended in a 0.5% methylcellulose aqueous solution. Each suspension (3, 10, 30 and 100 mg/kg/10 ml/day) was orally administered to an animal at the same time of each DNFB sensitization. The number of animals is 8 for each of a 3- and a 10-mg/kg/10 ml/day group, and 10 for each of a 30- and a 100-mg/kg/10 ml/day group in each of the active component and the allopurinol. As the control group, 10 ml/kg of 0.5% methylcellulose aqueous solution, the solvent for the active component and allopurinol, was administered to each of 8 sensitized animals.

The variations with time of the survival rate and the body weights of the mice administered with the agents were followed up to the 6th day after the final sensitization and recorded. For survived sensitized animals, a 0.3% DNFB acetone-olive oil (4:1) mixed solution (10 $\mu$l on each of the obverse and the reverse side of an ear) was applied on one ear to elicit an immune reaction and an acetone-olive oil (4:1) mixed solution (10 $\mu$l on each of the obverse and the reverse side of an ear) was applied on the other ear on the sixth day after the final sensitization. The ear thicknesses were measured with a dial thickness gauge (Ozaki Seisakusho, G-1A) before the elicitation, and 24 hr and 48 hr after the elicitation.

The variations of the body weights and the ear thicknesses were expressed as the mean ± standard deviation for each group. A significant difference test against the control group was carried out by Dunnett's multiple comparison test.

The variations of the survival rates with time after the administration of the agents are shown in FIGS. 4A and 4B (the day of the final sensitization is expressed as the date zero). As shown in FIG. 4A in the groups administered with the active component of the agent of the present invention, all animals were survived, excluding one animal of the 100 mg/kg/day group. In contrast with this, as shown in FIG. 4B the survival rate decreased dose-dependently with time from a low dose level in the allopurinol group.

The variations of the body weights of the survived animals with time after the administration of each agent are shown in FIGS. 5A and 5B (the day of the final sensitization is expressed as the date zero). As shown in FIG. 5A the phenylthiazole derivative, the active component of the agent of the present invention, did not produce a significant change on the body weights of the animals. In contrast with this, as shown in FIG 5B allopurinol decreased the body weights of the animals significantly at the doses of 30 and 100 mg/kg ($p<0.01$ and $p<0.05$, respectively).

Further, the variations of the ear thicknesses of the survived animals with time after the elicitation of immune reaction are shown in FIG. 6 (the hour of the elicitation of the immune reaction is expressed as the date zero). In the groups administered with the phenylthiazole derivative, the active component of the agent of the present invention, none of the effect in terms of the increase of the ear thicknesses was observed. In contrast with this, allopurinol stimulated the increase of the ear thicknesses, and the allergy reaction significantly at the dose of 30 mg/kg ($p<0.05$).

The results of Example 2 to Example 4 show that the agent of the present invention is effective as a protecting agent for an organ or a tissue in various kinds of diseases caused by e.g. the ischemia-reperfusion injury. Further, they indicate that the agent of the present invention is superior to the conventional xanthine oxidase inhibitor since it can suppress the generation of active oxygen from leukocytes through the inhibition of the production of a chemical mediator such as $LTB_4$ in addition to the above protective activity in the course of its expression. Furthermore, the agent is free from the aggravation of the allergic reaction and severe side effects including death, which are observed in allopurinol, a conventional xanthine oxidase inhibitor and a therapeutic agent for gout used now. Accordingly, it is concluded that the agent of the present invention has higher safety than allopurinol.

We claim:

1. A method of treating diseases associated with an ischemia-reperfusion injury of an organ, comprising administering a composition containing a phenylthiazole derivative expressed by the following formula (1) and/or its salt as an active ingredient

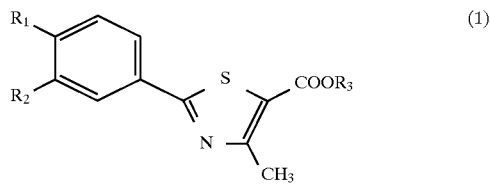

(1)

wherein $R_1$ is a $C_1-C_8$ alkoxy group or a cyclic amino group, $R_2$ is a cyano group or a nitro group and, $R_3$ is a hydrogen atom or a $C_1-C_4$ alkyl group.

2. A method of treating diseases associated with an ischemia-reperfusion injury of an organ caused by generation of active oxygen, comprising administering a composition containing a phenylthiazole derivative expressed by the following formula (1) and/or its salt as an active ingredient

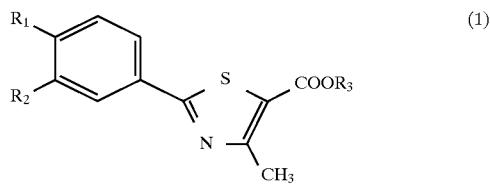

(1)

wherein $R_1$ is a $C_1-C_8$ alkoxy group or a cyclic amino group, $R_2$ is a cyano group or a nitro group and, $R_3$ is a hydrogen atom or a $C_1-C_4$ alkyl group.

3. A method of treating diseases associated with an ischemia-reperfusion injury of heart, liver, brain, kidney, digestive canals or lung caused by generation of active oxygen, comprising administering a composition containing a phenylthiazole derivative expressed by the following formula (1) and/or its salt as an active ingredient

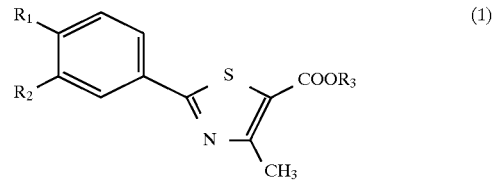

(1)

wherein $R_1$ is a $C_1-C_8$ alkoxy group or a cyclic amino group, $R_2$ is a cyano group or a nitro group and, $R_3$ is a hydrogen atom or a $C_1-C_4$ alkyl group.

4. A protecting method for diseases associated with an ischemia-reperfusion injury of an organ comprising administering a phenylthiazole derivative expressed by the following formula (1) and/or its salt as an active ingredient

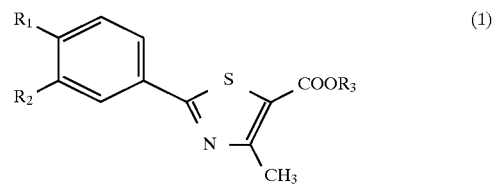

(1)

wherein $R_1$ is a $C_1-C_8$ alkoxy group or a cyclic amino group, $R_2$ is a cyano group or a nitro group and, $R_3$ is a hydrogen atom or a $C_1-C_4$ alkyl group.

5. A protecting method for diseases associated with an ischemia-reperfusion injury of an organ caused by the generation of active oxygen comprising administering a phenylthiazole derivative expressed by the following formula (1) and/or its salt as an active ingredient

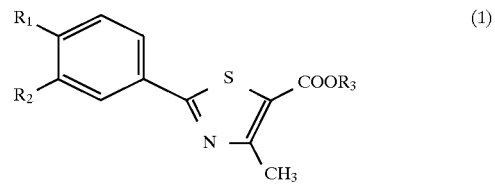

(1)

wherein $R_1$ is a $C_1-C_8$ alkoxy group or a cyclic amino group, $R_2$ is a cyano group or a nitro group and, $R_3$ is a hydrogen atom or a $C_1-C_4$ alkyl group.

6. A protecting method for diseases associated with an ischemia-reperfusion injury of heart, liver, brain, kidney, digestive canals or lung caused by the generation of active oxygen comprising administering a phenylthiazole derivative expressed by the following formula (1) and/or its salt as an active ingredient

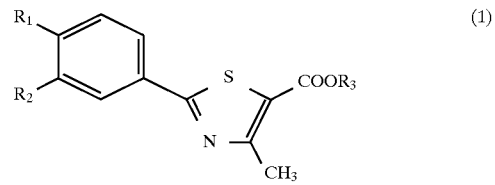

(1)

wherein $R_1$ is a $C_1-C_8$ alkoxy group or a cyclic amino group, $R_2$ is a cyano group or a nitro group and, $R_3$ is a hydrogen atom or a $C_1-C_4$ alkyl group.

* * * * *